(12) United States Patent
Doerr et al.

(10) Patent No.: US 8,649,877 B2
(45) Date of Patent: Feb. 11, 2014

(54) EXTENDED NOISE MODE

(75) Inventors: Thomas Doerr, Berlin (DE); Ingo Weiss, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 544 days.

(21) Appl. No.: 12/972,463

(22) Filed: Dec. 18, 2010

(65) Prior Publication Data

US 2011/0152973 A1 Jun. 23, 2011

Related U.S. Application Data

(60) Provisional application No. 61/288,862, filed on Dec. 22, 2009.

(51) Int. Cl.
*A61N 1/08* (2006.01)

(52) U.S. Cl.
USPC .......................................................... 607/62

(58) Field of Classification Search
USPC ................................. 607/4, 5, 9, 62
See application file for complete search history.

(56) References Cited

U.S. PATENT DOCUMENTS 5,697,958 A * 12/1997 Paul et al. ........................ 607/31
7,561,915 B1    7/2009 Cooke et al.
2006/0167496 A1    7/2006 Nelson et al.
2006/0293591 A1   12/2006 Wahlstrand et al.
2007/0203523 A1    8/2007 Betzold

OTHER PUBLICATIONS

European Search Report dated May 11, 2011 (8 pages).

* cited by examiner

*Primary Examiner* — Christopher D Koharski
*Assistant Examiner* — Frances Oropeza
(74) *Attorney, Agent, or Firm* — ARC IP Law, PC; Joseph J. Mayo

(57) ABSTRACT

A device and a method for working in the presence of electromagnetic fields, in particular fields occurring in cautery applications. Also relates to a partially implanted medical device (IMD), having a unit for detecting electromagnetic interference fields, at least one control unit, a timer, and a detection unit for electrical measured variables and/or a stimulation unit, at least one electrode line having an electrode at one end which is brought into contact with bodily tissue, and which either extends inside the body and/or is situated on the surface of an implant, wherein when nonphysiological signals and/or electromagnetic interference fields are detected and the unit for electromagnetic interference fields evaluates the detected signals as nonphysiological signals for a first specifiable time period, and/or for a second specified time period the stimulation unit is placed in an asynchronous operating state in which the wearer of the IMD is asynchronously stimulated.

14 Claims, 4 Drawing Sheets

EXTENDED NOISE MODE

This application claims the benefit of U.S. Provisional Patent Application 61/288,862, filed on Dec. 22, 2009, which is hereby incorporated by reference in its entirety.

BACKGROUND OF THE INVENTION

1. Field of the Invention

Embodiments of the invention relate to a device and a method for working in the presence of electromagnetic fields, in particular fields occurring in cautery applications.

2. Description of the Related Art

Although cautery applications are becoming increasingly important in medicine, particularly in surgical procedures and in conjunction with damaged vessels, such applications are contraindicated for some patients. Such contraindication may result from an at least partially implanted medical device (also referred to below as "implant" or "IMD"), in particular for so-called implanted cardiverter-defribillator (ICD) patients.

Cautery applications in the prior art primarily involve electrical cautery, i.e., cautery that is carried out using an object, for example a thin wire, which is heated by current flow. Cautery is also referred to as "diathermy". Distinctions are made among electrical high-frequency diathermy, ultrasonic diathermy, and microwave diathermy. Ultrasonic diathermy is generally considered to be noncritical for IMD wearers, whereas high-frequency diathermy and microwave diathermy may interfere with an IMD.

To still allow cautery applications, in particular using high-frequency diathermy and microwave diathermy, primarily asynchronous operating modes for pacemakers and ICD patients are known. These have the disadvantage that a considerable proarrhythmic risk results from asynchronous stimulation. Unnecessary asynchronous stimulation is contraindicated, especially for ICD patients.

Currently known interference detectors for all established pacemaker (IPG) and ICD systems cannot be used for this purpose, since such detectors depart from asynchronous interference mode immediately after onset of the interference. Thus, these detectors fail in the presence of pulsed interferences, which occur in cautery applications, among others.

BRIEF SUMMARY OF THE INVENTION

The object of one or more embodiments of the invention is to provide a device and a method for medical devices and implantable medical devices which eliminate the disadvantages of the prior art and allow safe operation in the presence of electromagnetic interference fields, in particular based on cautery applications. The object is achieved by an at least partially implantable medical device (IMD) having the features as claimed herein.

The at least partially implantable medical device (IMD) comprises at least the following: a unit for detecting electromagnetic interference fields, the unit having at least one sensor and/or indicator for electromagnetic interference fields, and/or being designed for detecting and identifying nonphysiological signals, at least one control unit which may be connected to the unit for detecting electromagnetic interference fields, at least containing a timer and a detection unit for electrical measured variables and/or at least containing a stimulation unit, at least one electrode line which may be connected to the control unit and/or to the unit for detecting electromagnetic interference fields, and which at the other end has an electrode which in the at least partially implanted state may be brought into contact with bodily tissue, and which either extends inside the body or which may be situated on the surface of an implant, whereby when nonphysiological signals and/or electromagnetic interference fields are detected the unit for electromagnetic interference fields evaluates the detected signals as nonphysiological signals for a first specifiable time period, and/or for a second specified time period the stimulation unit is placed in an asynchronous operating state in which the wearer of the IMD is asynchronously stimulated.

The IMD is preferably an implantable or external stimulator.

An external stimulator is understood to mean, for example, without being limited thereto, an external cardiac stimulator, external defibrillator, and/or neurostimulator, wherein for external stimulators portions may be implanted or temporarily implanted.

It is also preferred that the IMD is an implant for monitoring bodily functions, but is not limited to an implantable cardiac monitor. Such an implant may have electrode lines together with at least one electrode which extend into the body, and/or may have least one electrode on the implant surface for detecting physiological signals.

It is also preferred that the asynchronous operating state is activated for the second specified time period whenever at least one stimulation pulse has been emitted, with simultaneous detection of nonphysiological signals and/or with detection of electromagnetic interference fields.

It is further preferred that the asynchronous operating state is activated for the second specified time period whenever a predeterminable minimum number of nonphysiological signals is detected in a predeterminable time window.

It is also preferred that the asynchronous operating state is an A00, V00, or D00 operating state.

It is likewise preferred that the asynchronous operating state includes biventricular stimulation.

It is also preferred that the asynchronous operating state is associated with a change in the stimulation frequency, the asynchronous stimulation frequency being calculated from the heart rate before a detected electromagnetic interference and/or the detection of nonphysiological signals.

One possible method for calculating the asynchronous stimulation frequency from the heart rate before a detected electromagnetic interference and/or the detection of nonphysiological signals is to add a predeterminable number of heartbeats per time unit, such as but not limited to the heart rate +10 bpm.

It is further preferred that the asynchronous operating state is associated with a change in the stimulation amplitude and/or the stimulation pulse width.

It is also preferred that detected signals are evaluated as nonphysiological signals, and/or the asynchronous operating state may be activated for only a specifiable first time period by the detection of nonphysiological signals and/or electromagnetic interference fields.

It is particularly preferred that the specifiable first time period is in a range of hours and/or days.

It is likewise preferred that the unit for detecting electromagnetic interference fields includes at least one of the following sensors or indicators: GMR sensor, MagFET sensor, Hall sensor, electro-optical converter as indicator, monitoring of battery voltages during capacitor charging processes as indicator, detection of RF fields as indicator, detection of magnetic gradient fields as indicator, and detection of currents induced by electromagnetic fields as indicator.

The object is achieved by use of a method for working in the presence of electromagnetic interference fields which are detectable by an IMD, whereby when nonphysiological signals and/or electromagnetic interference fields are detected, for a first specifiable time period the detected signals are evaluated as nonphysiological signals, and/or for a second specified time period the stimulation unit is placed in an asynchronous operating state in which the wearer of the IMD asynchronously stimulated. The method may be carried out using any of the above-referenced IMDs, for example.

BRIEF DESCRIPTION OF THE DRAWINGS

Several aspects of the invention are illustrated in FIGS. 1 through 4.

DETAILED DESCRIPTION OF THE INVENTION

In one example the system according to the invention is implemented in a pacemaker. For the case of pulsed interference, it is possible that patients dependent on pacemakers may not be stimulated continuously, since conventional noise detection for ICD/IPG departs from interference mode immediately after the interference ends. However, to ensure stimulation during a cautery application, in this case an extended interference mode is implemented which includes an additional timer, thereby extending the time of an asynchronous stimulation after a one-time interference detection. By means of prior programming, this time is matched to the typical duration of the procedure. This interference mode may be restricted with respect to time, such as but not limited to hours, days, or weeks.

In another example the extended interference mode is implemented in a cardiac monitor, which during a pulsed interference possibly may not continuously record heart signals, and/or which labels the identified interferences to prevent misinterpretation of the recorded data. The interference mode is maintained until no further interferences have been detected after a presettable time period.

Figure 1:
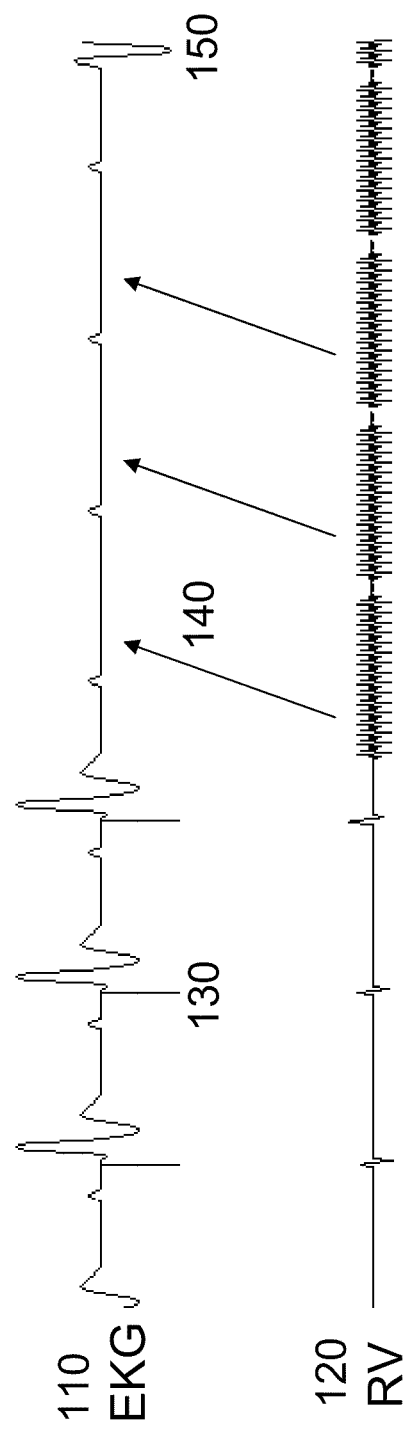
FIG. 1 shows a schematic illustration of the starting situation for pulsed interferences.

FIG. 1 illustrates a typical situation with the prior art. In this case the stimulation of a pacemaker is erroneously inhibited by the pulsed interference fields of magnetic resonance tomography (MRT), resulting in underprovision of the patient.

Illustrated here is the surface EKG 110 and the (optically transmitted) intracardial right ventricular electrogram 120 of a dual-chamber pacemaker for a patient with total AV block.

Before the onset of the MRT interference the patient receives synchronous atrial stimulation 130. However, these stimulation pulses are routinely inhibited by the pulsed interference 140. This repeated inhibition occurs because the interference is constantly interrupted, thus preventing the pacemaker from switching to an interference mode.

In this example the patient still has a very slow ventricular escape rhythm 150, indicating a minimal pump function of the ventricle. Without this escape rhythm, in the present case cardiac arrest would occur. Besides this possibility, also prior to a cautery application, for example, the stimulator may be placed in an asynchronous stimulation mode which, however, entails increased risk of tachycardia.

Figure 2:
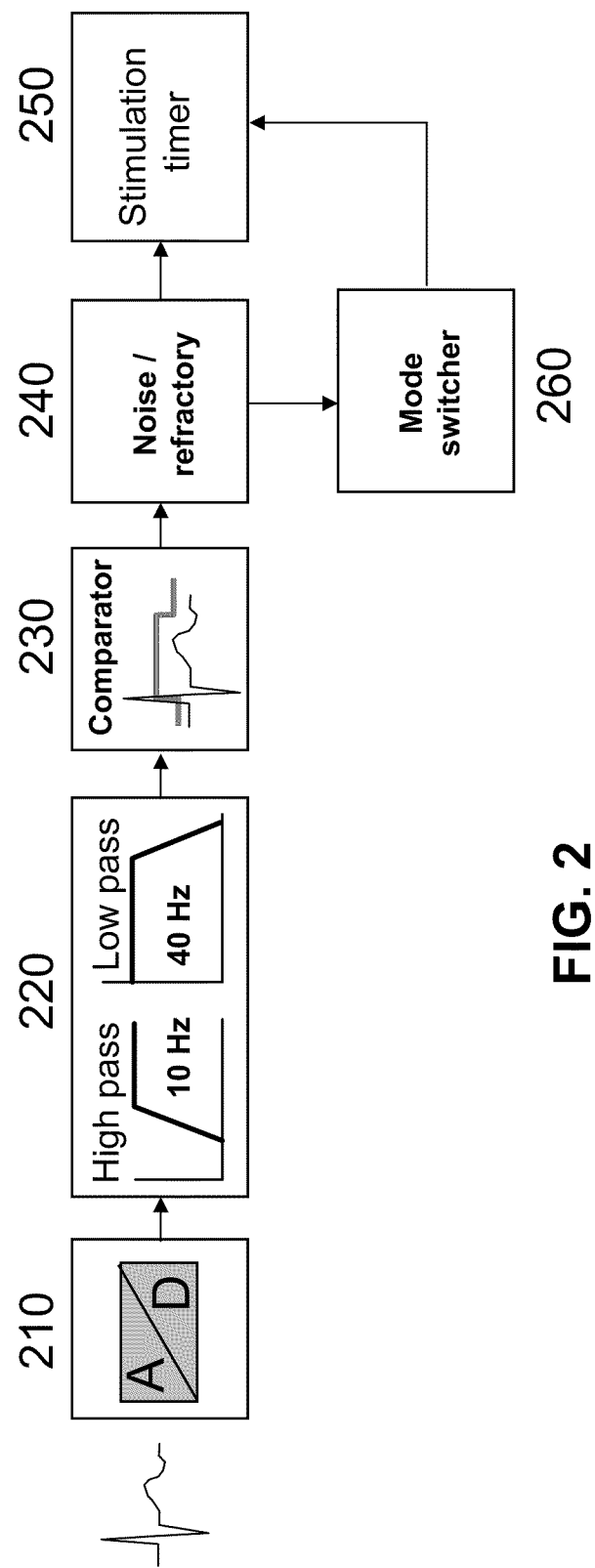
FIG. 2 shows a block diagram of a cardiac stimulator according to the invention.

FIG. 2 shows the block diagram of an enhanced cardiac stimulator according to the invention. The IEGM signals are first amplified and digitized 210, and are then conditioned in a digital filter unit 220 for the subsequent signal processing. The sensed events are generated in an adaptive comparator stage 230 and then sent to the noise and refractory elements 240. The signals evaluated in this manner are sent to the stimulation timer 250, and the pacemaker stimulation is controlled using this information.

According to the invention, the block diagram includes an additional mode switcher 260 which is controlled via a connection of the noise evaluation unit 240, and which switches the stimulation timer 250 to an asynchronous stimulation mode (V00, D00) for a programmed period of time whenever noise events have occurred.

Figure 3:
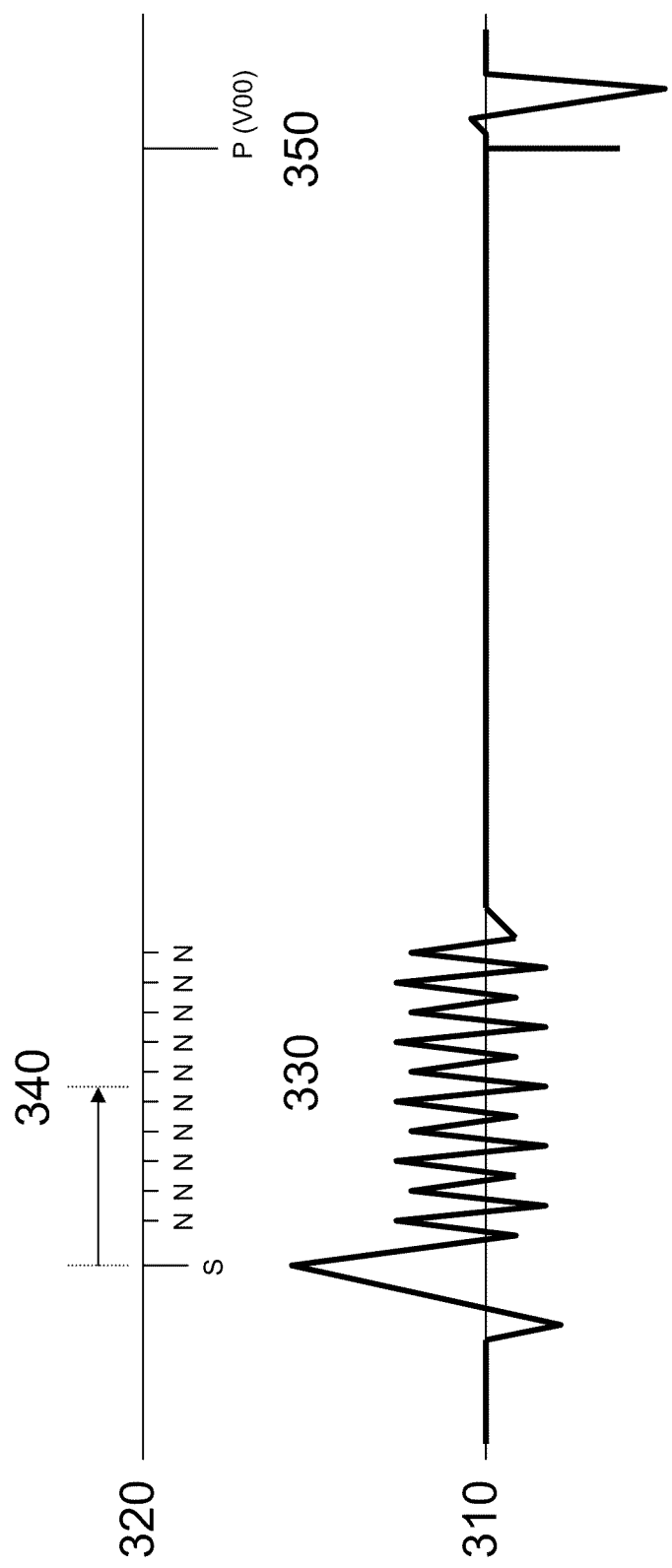
FIG. 3 shows a schematic illustration of the control of the mode switcher illustrated in FIG. 2.

FIG. 3 shows an example of a timing diagram; i.e., FIG. 3 shows the control of the mode switcher shown in FIG. 2. The intracardial IEGM channel 310 and the marker channel 320 are illustrated. In this example, an interference 330 appears after a sensed R wave (S). The interference 330 is identifiable in the marker channel on the basis of the noise markers (N). If the duration of an uninterrupted noise state exceeds a settable time period 340, the mode switcher 260 signals the stimulation timer 250 to switch to asynchronous stimulation 350.

By the introduction of the required noise duration 340 a distinction may be made between multiple triggering of an R wave (which is also briefly evaluated as noise) and a relevant pulsed interference which makes mode switching necessary.

Figure 4:
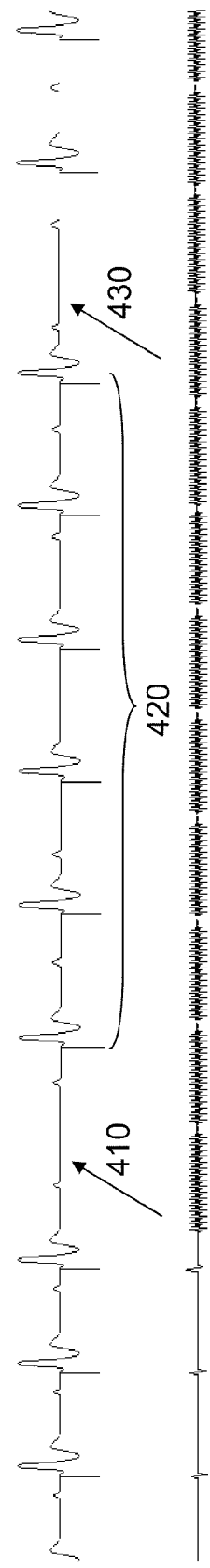
FIG. 4 shows an example of a situation using the approach according to the invention.

FIG. 4 shows the example illustrated in FIG. 1, this time with the interference switching according to the invention. Here as well, the ventricular stimulation is initially inhibited by the onset of MRT interference 410. However, the implant then automatically switches to a programmed interference mode, in this case a V00 stimulation 420, for six cycles. This is followed by automatic switching back to the original DDD operating mode. Since the interference is still present, further stimulation is inhibited 430, and a switch is once again made to V00 mode for six cycles.

It is thus possible to achieve reliable backup stimulation for pulsed interferences, which does not expose the patients to asynchronous stimulation for a long time period.

The number of cycles and/or the duration of the asynchronous stimulation may be correspondingly varied.

In principle, implants and methods according to the invention are selected independently of the detection and identification methods for the pulsed interference sources. For implants, however, on the one hand the most accurate detection methods possible and on the other hand the lowest possible energy requirements are preferred. This results in use of the following as advantageous detection and/or identification possibilities: GMR sensors, MagFET sensors, Hall sensors, electro-optical converters, monitoring of battery voltages during capacitor charging processes, detection of RF fields, detection of magnetic gradient fields, and detection of currents induced by electromagnetic fields. The technology is preferably implemented in conjunction with other technologies, such as but not limited to magnetic resonance tomography (MRT) detection and MRT-safe operation, to be able to make use of synergy effects. Thus, the methods and/or detection devices may be used for various applications.

It is thus possible to ensure reliable stimulation also for pulsed electromagnetic interferences, thereby allowing cautery applications to be used for pacemaker and ICD systems without having to program an asynchronous stimulation operating mode beforehand. Other applications using pulsed electromagnetic interferences are also possible which occur, for example, when electromagnetic radio frequency fields and/or gradient fields are used.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. At least partially implantable medical device comprising
   a unit configured to detect electromagnetic interference fields, wherein said unit comprises
      at least one sensor or indicator configured to
         detect electromagnetic interference fields and
         detect and identify nonphysiological signals;
   at least one control unit connected to the unit configured to detect electromagnetic interference fields, comprising
      a timer and
      a detection unit for electrical measured variables and
      a stimulation unit;
   at least one electrode line comprising a first end and a second end,
      wherein said at least one electrode line is connected at said first end to the at least one control unit and to the unit configured to detect electromagnetic interference fields,
      said second end opposite the first end comprises an electrode configured to be in contact with bodily tissue, and
      wherein said at least one electrode line is configured to extend inside a body and be situated on a surface of the least partially implantable medical device;
   wherein said unit configured to detect electromagnetic interference fields is further configured to
      evaluate the detected signals as nonphysiological signals for a first specifiable time period, and
      for a second specified time period, the stimulation unit is configured to be placed in an asynchronous operating state such that a wearer of the at least partially implantable medical device is asynchronously stimulated, when nonphysiological signals and electromagnetic interference fields are detected;
         wherein the asynchronous operating state is activated for the second specified time period whenever at least one stimulation pulse has been emitted, with simultaneous detection of nonphysiological signals, or with detection of electromagnetic interference fields or with both simultaneous detection of nonphysiological signals and with detection of electromagnetic interference fields.

2. The at least partially implantable medical device according to claim 1, wherein the at least partially implantable medical device is an implantable or external stimulator.

3. The at least partially implantable medical device according to claim 1, wherein the asynchronous operating state is activated for the second specified time period whenever a predeterminable minimum number of nonphysiological signals is detected in a predeterminable time window.

4. The at least partially implantable medical device according to claim 1, wherein the asynchronous operating state is an A00, V00, or D00 operating state.

5. The at least partially implantable medical device according to claim 1, wherein the asynchronous operating state includes biventricular stimulation.

6. The at least partially implantable medical device according to claim 1, wherein the asynchronous operating state is associated with a change in stimulation frequency, wherein asynchronous stimulation frequency is calculated from a heart rate before a detected electromagnetic interference and detection of said nonphysiological signals.

7. The at least partially implantable medical device according to claim 1, wherein the asynchronous operating state is associated with a change in a stimulation amplitude, change in a stimulation pulse width, or any combination thereof.

8. The at least partially implantable medical device according to claim 1, wherein the detected signals are evaluated as said nonphysiological signals, and the asynchronous operating state is activated for only a specifiable time period by detection of nonphysiological signals and electromagnetic interference fields.

9. The at least partially implantable medical device according to claim 8, wherein the specifiable first time period is in a range of hours, days, or any combination thereof.

10. The at least partially implantable medical device according to claim 1, wherein the unit configured to detect electromagnetic interference fields includes at least one of the following sensors or indicators:
    GMR sensor,
    MagFET sensor,
    Hall sensor,
    electro-optical converter,
    battery voltage sensor configured to monitor voltage during capacitor charging,
    RF field detector,
    magnetic gradient field detector,
    current detector for currents induced by electromagnetic fields.

11. The at least partially implantable medical device according to claim 6, wherein said asynchronous stimulation frequency calculated from a heart rate includes adding a predeterminable number of heartbeats per time unit to the heart rate.

12. A method comprising:
    detecting electromagnetic fields via an at least partially implantable medical device;
    wherein said at least partially implantable medical device continues to work in the presence of said electromagnetic fields; and wherein said partially implantable medical device comprises
       a unit configured to detect electromagnetic interference fields, wherein said unit comprises at least one sensor or indicator configured to
          detect electromagnetic interference fields and detect and identify nonphysiological signals;
    at least one control connected to the unit configured to detect electromagnetic interference fields, comprising
       a timer and
       a detection unit for electrical measured variables and
       a stimulation unit;
    at least one electrode line comprising a first end and a second end,
       wherein said at least one electrode line is connected at said first end to the at least one control unit and to the unit configured to detect electromagnetic interference fields,
       said second end opposite the first end comprises an electrode configured to be in contact with bodily tissue, and
       wherein said at least one electrode line is configured to extend inside a body and be situated on a surface of the least partially implantable medical device;

wherein said unit configured to detect electromagnetic interference fields is further configured to
evaluate the detected signals as nonphysiological signals for a first specifiable time period, and
for a second specified time period, the stimulation unit is configured to be placed in an asynchronous operating state such that a wearer of the at least partially implantable medical device is asynchronously stimulated, when nonphysiological signals and electromagnetic interference fields are detected;
wherein the asynchronous operating state is activated for the second specified time period whenever at least one stimulation pulse has been emitted, with simultaneous detection of nonphysiological signals, or with detection of electromagnetic interference fields or with both simultaneous detection of nonphysiological signals and with detection of electromagnetic interference fields.

13. The method of claim 12, wherein the asynchronous operating state is associated with a change in stimulation frequency, wherein asynchronous stimulation frequency is calculated from a heart rate before a detected electromagnetic interference and detection of said nonphysiological signals.

14. At least partially implantable medical device comprising
a unit configured to detect electromagnetic interference fields, wherein said unit comprises
at least one sensor or indicator configured to
detect electromagnetic interference fields and
detect and identify nonphysiological signals;
at least one control unit connected to the unit configured to detect electromagnetic interference fields, comprising
a timer and
a detection unit for electrical measured variables and
a stimulation unit;
at least one electrode line comprising a first end and a second end,
wherein said at least one electrode line is connected at said first end to the at least one control unit and to the unit configured to detect electromagnetic interference fields,
said second end opposite the first end comprises an electrode configured to be in contact with bodily tissue, and
wherein said at least one electrode line is configured to extend inside a body and be situated on a surface of the least partially implantable medical device;
wherein said unit configured to detect electromagnetic interference fields is further configured to
evaluate the detected signals as nonphysiological signals for a first specifiable time period, and
for a second specified time period, the stimulation unit is configured to be placed in an asynchronous operating state such that a wearer of the at least partially implantable medical device is asynchronously stimulated, when nonphysiological signals and electromagnetic interference fields are detected;
wherein the asynchronous operating state is activated for the second specified time period whenever at least one stimulation pulse has been emitted, with simultaneous detection of nonphysiological signals, or with detection of electromagnetic interference fields or with both simultaneous detection of nonphysiological signals and with detection of electromagnetic interference fields; and,
wherein the asynchronous operating state is associated with a change in stimulation frequency, wherein asynchronous stimulation frequency is calculated from a heart rate before a detected electromagnetic interference and detection of said nonphysiological signals, wherein the asynchronous operating state is activated for the second specified time period whenever a predeterminable minimum number of nonphysiological signals is detected in a predeterminable time window, and wherein said asynchronous stimulation frequency calculated from a heart rate includes adding a predeterminable number of heatbeats per time unit to the heart rate.

* * * * *